United States Patent
Gomez, Jr. et al.

(10) Patent No.: US 8,435,201 B2
(45) Date of Patent: May 7, 2013

(54) METHOD FOR TREATING A USER'S BACK OR NECK USING A TRACTION SYSTEM

(76) Inventors: Jose Gomez, Jr., Humble, TX (US); Victor B. Ramos, Houston, TX (US)

( * ) Notice: Subject to any disclaimer, the term of this patent is extended or adjusted under 35 U.S.C. 154(b) by 656 days.

(21) Appl. No.: 12/619,279

(22) Filed: Nov. 16, 2009

(65) Prior Publication Data
US 2011/0118642 A1 May 19, 2011

(51) Int. Cl.
*A61F 5/02* (2006.01)
*A61F 5/24* (2006.01)
*A61F 5/28* (2006.01)
*A61F 5/32* (2006.01)
*A61F 13/00* (2006.01)
*A61H 1/00* (2006.01)
*A41D 13/00* (2006.01)

(52) U.S. Cl.
USPC ............ 602/33; 602/32; 602/34; 602/35; 602/36; 128/97.1; 128/106.1; 128/107.1; 128/116.1; 601/24; 601/39; 2/44; 2/45; 2/69

(58) Field of Classification Search .......... 128/97.1, 128/106.1, 107.1, 116.1; 601/24, 39; 297/112, 297/218.1, 291.1; 602/32–36; 2/44, 45, 2/69

See application file for complete search history.

(56) References Cited

U.S. PATENT DOCUMENTS

| | | | | |
|---|---|---|---|---|
| 4,397,046 | A | * | 8/1983 | Steiner .................................. 2/44 |
| 5,007,413 | A | * | 4/1991 | Aalvik Thune .................. 602/18 |
| 6,258,050 | B1 | * | 7/2001 | Henderson ....................... 602/33 |
| 7,137,961 | B2 | * | 11/2006 | Hurd ................................ 602/32 |
| 2008/0066233 | A1 | | 3/2008 | Russell |
| 2008/0150337 | A1 | * | 6/2008 | Bilak et al. ................. 297/230.1 |
| 2009/0198163 | A1 | * | 8/2009 | Senyei et al. .................... 602/18 |

* cited by examiner

*Primary Examiner* — Patricia Bianco
*Assistant Examiner* — Nihir Patel
(74) *Attorney, Agent, or Firm* — Buskop Law Group, PC; Wendy Buskop

(57) ABSTRACT

A method for treating a user's back, a user's neck, or combinations thereof. The method can include the steps of: inserting a traction device into a pouch of a fabric garment; disposing the fabric garment over a user; engaging the traction device with a surface; and applying a pressure to the traction device using the user's back. The traction device can provide a therapeutic pressure to the user's back, to the user's neck, or to combinations thereof. The method can use a customizable traction device having a shearable fraction head and body. The shearable traction head and body can each be cut to a custom size to fit a user. The method can use a removable fabric chair cover disposed over a chair. A user can sit on the chair and apply a pressure to the traction device using the user's back.

15 Claims, 13 Drawing Sheets

(12A)

| USING A TRACTION HEAD THAT IS A SHEARABLE TRACTION HEAD, USING A TRACTION BODY THAT IS A SHEARABLE TRACTION BODY, CUTTING THE SHEARABLE TRACTION HEAD AND BODY TO CUSTOM SIZES TO FIT THE USER; AND DISPOSING THE SHEARABLE TRACTION BODY WITHIN THE POUCH | 210 |

| USING A TRACTION HEAD AND A TRACTION BODY HAVING DIFFERENT INDENTION LOAD DEFLECTIONS | 211 |

FIGURE 12B

METHOD FOR TREATING A USER'S BACK OR NECK USING A TRACTION SYSTEM

FIELD

The present embodiments generally relate to a method for treating a user's back, a user's neck, or combinations thereof using a fraction system, for providing therapeutic relief to a user.

BACKGROUND

A need exists for a method for treating a user's back or neck that can use a traction system and can be an alternative to surgery.

A need exists for a method for treating a user's back or neck that can be utilized in various locations and can use a transportable traction system.

A further need exists for a method for treating a user's back or neck that can use a traction system that is customizable for use by any sized or shaped user.

The present embodiments meet these and other needs.

BRIEF DESCRIPTION OF THE DRAWINGS

The detailed description will be better understood in conjunction with the accompanying drawings as follows:

FIGS. 12A-12B shows a diagram of another illustrative embodiment of the method.

Figure 1:
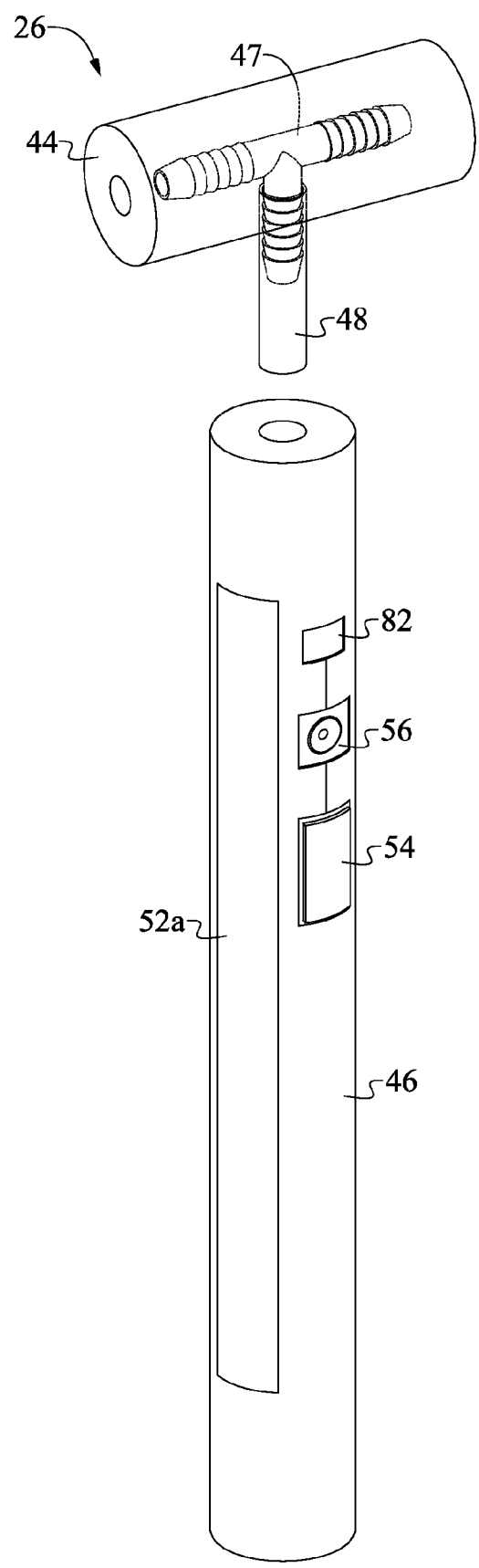
FIG. 1 shows an embodiment of a traction device.

The present embodiments are detailed below with reference to the listed Figures.

DETAILED DESCRIPTION OF THE EMBODIMENTS

Before explaining the present method in detail, it is to be understood that the method is not limited to the particular embodiments and that it can be practiced or carried out in various ways.

The present embodiments relate to a method for providing therapeutic relief to a user's back, neck, or combinations thereof. The method can use a wearable ambulatory traction system or a removable chair supported traction system.

Embodiments of the invention can provide a user with an alternative to surgery by providing therapeutic stress relief and relaxation to users experiencing muscular or skeletal pains, tension, or other muscular or skeletal ailments.

Embodiments can provide a user with an economical alternative to costly professional physical therapy. Embodiments of the method can use a traction system that can be low cost to manufacture.

Embodiments can decompresses stress in a user's back, neck, or combinations thereof; therefore providing the user with greater flexibility.

Embodiments can relieve muscular tension; thereby leading to faster recovery from muscle cramps, aches, and pains.

Embodiments can remind a user to maintain proper posture.

Embodiments of the method can use a traction system that can be transportable and can be utilized anywhere there is a generally flat surface or a chair.

Embodiments of the method can use a traction system that can be lightweight and customizable such that the traction system can be used by users of any age, size, shape, weight, or height.

Embodiments of the method can use a traction system that can be washable, durable, and flexible.

Traction systems usable with the method can include a traction device which can be a cushion. The traction device can include a fraction head, a fraction body; and a centralizer. In embodiments, the traction head and body can be substantially tubular. The traction head can engage with the traction body at an angle, which can be a right angle.

The traction device can have a coating disposed about it. The coating can be a water-proof or a water resistant coating that can resist the penetration of sweat from a user's body.

In embodiments, the traction head and the traction body can both be cylindrically shaped and can have identical diameters.

The traction head can have a diameter different from a diameter of the traction body.

Each traction head or body can be a foam traction head or body, or can be a closed cell foam traction head or body. The traction head and traction body can be made of polypropylene, polyethylene, polyurethane, an extruded foam polymer, a memory foam such as a visco-elastic polyurethane memory foam, or another foam polymer.

The fraction head can have a support member for engaging the centralizer. The support member can be disposed within the traction head. The support member can have a left tube axially aligned with the traction head, a right tube axially aligned with the fraction head, and a central tube disposed transverse to the left and right tubes.

The central tube can engage the centralizer. The support member can provide a sturdy engagement between the traction head and the fraction body. The centralizer can extend from the traction head and engage the traction body, providing the engagement between the fraction head and the traction body. The centralizer can centrally engage the traction body. In embodiments, the centralizer can be formed as a substantially tubular member and can be hollow.

In embodiments, a heating element or a cooling element can be disposed within the traction head or the traction body, allowing a user to adjust a temperature of the traction device.

In embodiments, the centralizer can be a flexible centralizer that can extend from the traction head and can engage the traction body, providing a flexing engagement between the traction body and the fraction head. The centralizer can be a removable from the traction head and can be elastic.

Embodiments of traction systems usable in the method can also include a fabric garment which can have a front portion for covering a front portion of a user's body and a back portion for covering a back portion of the user's body. The fabric garment can be a wearable fabric garment.

The fabric garment can be any number of fabric garments including but not limited to: a sheath, a shirt, a backpack, a v-neck shirt, a T-shirt, a long sleeved shirt, a vest, a cardigan, a hoodie, a jacket, a poncho, a coat, a sweater, or a robe.

Embodiments of tractions systems usable in the method can include a pouch. The pouch can be secured to the fabric garment, such as to the back portion of the fabric garment. The pouch can include an opening for receiving the traction body and the traction head. The traction body and the traction head can be insertable into the pouch. The pouch can contain the traction body in a removable engagement. In embodiments, the pouch can be a closable pouch. The pouch can be rectangular in shape with dimensions of about eleven inches by about twenty two inches.

Embodiments of the method can use a system that can include a removable fabric chair cover having a front portion and a back portion for covering a chair. The removable fabric chair cover can be disposed over a back portion of a chair.

The removable fabric chair cover can be any number of fabric covers including but not limited to: a shirt, a pillow case, a sleeve, a bag, a sheath, a cover, or a fabric loop.

The chair can be: an airplane seat, an automobile seat, a truck seat, a folding stadium seat, an office chair, a movie theater seat, an auditorium seat, a folding chair, a lawn chair, a dining room chair, a motor cycle high-back chair seat, a tractor chair, a vehicle seat, or another seat. It is contemplated that the chair can be any type of chair, seat, or similar device.

In embodiments, the pouch can be sewn onto the fabric garment or the removable fabric chair cover. The pouch can also be removably attached to the fabric garment or the removable fabric chair cover such as by using Velcro™ or another type of removable attachment. The pouch can be secured to an inside surface of the fabric garment or the removable fabric chair cover and the traction body can be insertably engaged within the pouch.

In embodiments, the fabric garment can be worn by a user. The user's back can be used to apply a pressure to the traction device while the traction device is also engaged with a surface, thereby allowing the fraction device to provide a therapeutic pressure to the user's back, to the user's neck, or to combinations thereof. The surface can be the surface of a bed.

Embodiments of traction systems usable with the can be ambulatory. A user can move and walk about while wearing the fabric garment with the traction device inserted into the pouch. A user can therefore go from using the system at home, to using the system at work, then to using the system at another location; all while continuously wearing the fabric garment without having to remove the fabric garment.

A user can interchange the traction device with different fabric garments or removable fabric chair covers, each having a pouch. For example, a user can a have a single traction device that the user can use with a fabric garment that is a dress shirt while the user is at work. When the user goes home from work, the user can remove the traction device from the pouch of the dress shirt fabric garment and can insert the traction device into a pouch of a t-shirt fabric garment. At night, the user can remove the traction device from the pouch of the t-shirt fabric garment and can insert the traction device into a pouch of a robe or a pajamas fabric garment. A user can therefore use the traction device throughout an entire day with various fabric garments.

In embodiments of the method, the removable fabric chair cover can be disposed over a chair. A user can sit on the chair with the traction device in the pouch disposed between the user and the chair. The user's back can be used to apply a pressure to the traction device while the traction device is also engaged with the chair, thereby allowing the fraction device to provide a therapeutic pressure to the user's back, to the user's neck, or to combinations thereof.

Embodiments of the method can use a system that can be transportable. A user can transport the removable fabric chair cover with the traction device inserted into the pouch. A user can therefore go from using the system at home, to using the system at work, then to using the system at another location.

A user can interchange the traction device with different removable fabric chair covers, each having a pouch. For example, a user can a have a single traction device that the user can use with a first removable fabric chair cover while the user is at work. When the user goes home from work, the user can remove the traction device from the pouch of the first removable fabric chair cover and can insert the traction device into a pouch of a second removable fabric chair cover. A user can therefore use the traction device throughout an entire day with various removable fabric chair covers.

The pressure applied by the user's back can be applied for a predetermined time interval. A predetermined time interval can be an amount of time a user determines to apply the pressure. The predetermined time interval can be variable and can be any amount of time chosen by the user.

The pressure applied by the user's back can be a variable user-specified pressure. The user can vary the pressure using a weight of a portion of the user's body that is in engagement with the traction device. A user can vary the pressure by applying more or less pressure to the traction device using the user's back.

A user can apply pressure in a series of pressure cycles to provide a decompressive therapeutic pressure to the user's back.

The engagement between the traction head and the traction body can be at a variable angle. In embodiments, the variable angle can range from about 83 degrees to about 97 degrees.

Embodiments of the system can be adjusted during use. The variable angle can allow a user to adjust the angle of the engagement of the fraction head to the traction body to accommodate a position of the user's neck. For example, during use if a user leans or bends the user's neck, the variable angle can allow the traction head to bend along with the user's neck; providing support and therapy to the user's neck even when the user's neck is bent.

In embodiments, the traction device, the fabric garment, or the removable fabric chair cover can include a message portion. The message can be an advertisement, a slogan, a logo such as a sports logo, an instruction explaining how to use the system, an identification of the product, a telephone number, a website address, a personal message, a photo, or another message.

Embodiments can include a pressure sensor disposed within or on the traction device. The pressure sensor can be in communication with an alarm which can also be disposed within or on the traction device. A preset pressure limit can be a maximum pressure that a user determines should be applied to the traction device by the user's back. The pressure sensor can measure the pressure applied by a user's back and when the pressure applied by the user's back exceeds the preset pressure limit, the pressure sensor can send a signal to the alarm to provide an alert to the user.

The invention can include a time sensor which can be actuated and begin measuring time when a user applies pressure to the traction device. When the user ceases to apply pressure to the traction device, the time sensor can stop measuring time. A preset time limit can be a maximum time that a user determines pressure should be applied to the traction device by the user's back. The time sensor can measure the usage time in which pressure is applied by a user's back, and when the usage time exceeds the preset time limit, the time sensor can send a signal to the alarm to provide an alert to the user.

The alarm can provide the alert to the user when the pressure applied by the user's back is greater than a preset pressure limit; when a usage time is greater than a preset time limit; or combinations thereof.

In embodiments the pressure sensor, the time sensor, and the alarm can be in communication with a processor which can be in communication with a data storage. The preset pressure and time limits can be stored on the data storage and can be reprogrammed or adjusted to accommodate various different users.

The data storage can have computer instruction stored on it. The computer instructions can include: computer instructions to compare measured pressure applied by a user's back to the preset pressure limit; computer instructions to compare measured time to the preset time limit; computer instructions to provide an alarm; or combinations thereof.

In embodiments, the fraction device can have a vibration member disposed on it that can produce vibrations for relaxing a user.

In embodiments, fraction systems usable with the method can be customizable wearable ambulatory traction systems that can include a traction device that can be a customizable traction device.

Users of various ages can have various sizes, shapes, and heights. The customizable traction device allows a user to custom a size of the traction device such that it fits the user's body, allowing a wide variety of users to use the system.

The customizable traction device can include a traction head and body that can be a shearable traction head and a shearable traction body which can each be cut to a custom size by the user.

The shearable traction head and body can each have a plurality of dimensional indicators disposed about them. The dimensional indicators can provide the user with indications of where to shear or cut the fraction head or body such that the traction head or body is custom sized to fit the particular user. The traction body can be sheared or cut to fit a length of a particular user's spine.

The customizable wearable ambulatory traction system can be formed substantially the same as the wearable ambulatory traction system with the exception of replacing the fraction device with the customizable traction device.

The customizable wearable ambulatory traction system usable with the method can include a centralizer formed as described above, and extending from the shearable traction head and engaging the shearable traction body; providing an engagement between the shearable traction head and the shearable traction body.

The customizable wearable ambulatory traction system usable with the method can include a fabric garment or a removable fabric chair cover and a pouch secured to the fabric garment or the removable fabric chair cover, each formed substantially as described above. The pouch can securely contain at least a portion of the shearable traction body.

The customizable traction device can be engaged with a surface such that a pressure is applied to the customizable traction device using the user's back. The customizable traction device can provide a therapeutic pressure to the user's back, the user's neck, or combinations thereof.

In embodiments of the traction head and traction body can each have an indention load deflection ranging from about 10 pounds to about 80 pounds, however it is contemplated that the traction head and body can have other indention load deflections.

The 25 percent indention load deflection measurement of a traction head or body is measured by indenting or compressing the traction head or body by 25 percent of its original height. The amount of force, in pounds, required to indent the traction head or body is equal to the 25 percent indention load deflection. The more force required to compress the traction head or body, the firmer the traction head or body.

Embodiments of the traction device usable with the method can include a fraction head with one indention load deflection and a traction body with another indention load deflection. For example, a user might require a softer traction body for placement behind the user's back and/or spine and a harder traction head for placement behind the user's neck. For such uses, the traction device can have a traction head with a higher indention load deflection, such as 40 pounds, and a traction body with a lower indention load deflection, such as 18 pounds. Alternatively, the user can have a traction body with a higher indention load deflection, such as 40 pounds, and a traction head with a lower indention load deflection, such as 18 pounds.

Embodiments of the traction body and traction head usable with the method can have a density of 1.5 pounds per cubic foot. However, it is contemplated that the traction head and body can have other densities as well.

The traction device can be customizable, wherein various sizes of traction heads with various indention load deflections can be interchangeable, and can be used with various sizes and of interchangeable traction bodies with various indention load deflections.

The traction body can have a length that can vary from about twelve inches to about thirty inches, however it is contemplated that the traction body can be other lengths. The traction head can have a length that can vary from about five inches to about seven inches, however it is contemplated that the traction head can be other lengths. The traction head and body can each have a diameter that can vary from about two inches to about five inches.

Embodiments of the method for treating a user's back, a users neck, or combinations thereof can include positioning a fabric garment about a user's body or positioning a removable fabric chair cover about a chair.

Next, a traction device having a traction head and a traction body can be positioned in a pouch of the fabric garment or in a pouch of the removable fabric chair cover.

Another step can include attaching the traction head to the traction body using a removable flexible elastic centralizer, allowing the traction head to transversely engage the traction body at an angle which can vary during use.

Next, the traction device can be engaged with a surface.

A next step can include applying a pressure to the traction device using the user's back for a predetermined time interval, producing a decompressive force on the user's back, the user's neck, or combinations thereof.

The method can include the step of predetermining a time interval and applying the pressure to the traction device for the predetermined time interval. The method can include using a predetermined time interval that is from about 5 minutes to about 30 minutes after awaking from a nights sleep, to relieve stress on a user's back or user's neck prior to walking. The method can include using a predetermined time interval that is for an entire evening's sleep.

The method can include the step of coating the traction device to prevent the absorption of sweat or other liquids by the traction device.

The method can include the step of disposing a message on the traction device, the fabric garment, or the removable fabric chair cover.

The method can include the step of using a foam traction head having a diameter different from the foam traction body.

The method can include the steps of: using a pressure sensor to measure the pressure applied by the user's back; using a time sensor to measure a usage time by the user; providing an alert using an alarm in communication with the pressure and time sensors. An alert can be provided to the user: when the pressure is greater than a preset pressure limit; when a usage time is greater than a preset time limit; or combinations thereof.

Turning now to the Figures, FIG. 1 shows an embodiment of a traction device 26 usable with the method. The traction device is shown with a traction head 44 and a traction body 46.

A centralizer 48 is shown extending from the traction head and engaging the traction body. The centralizer is also shown in engagement with a support member 47. The support member is shown disposed within the traction head.

A pressure sensor 54 and a time sensor 82 are shown disposed on the traction body and are both in communication with an alarm 56. Also shown is a message portion 52a.

Figure 2:
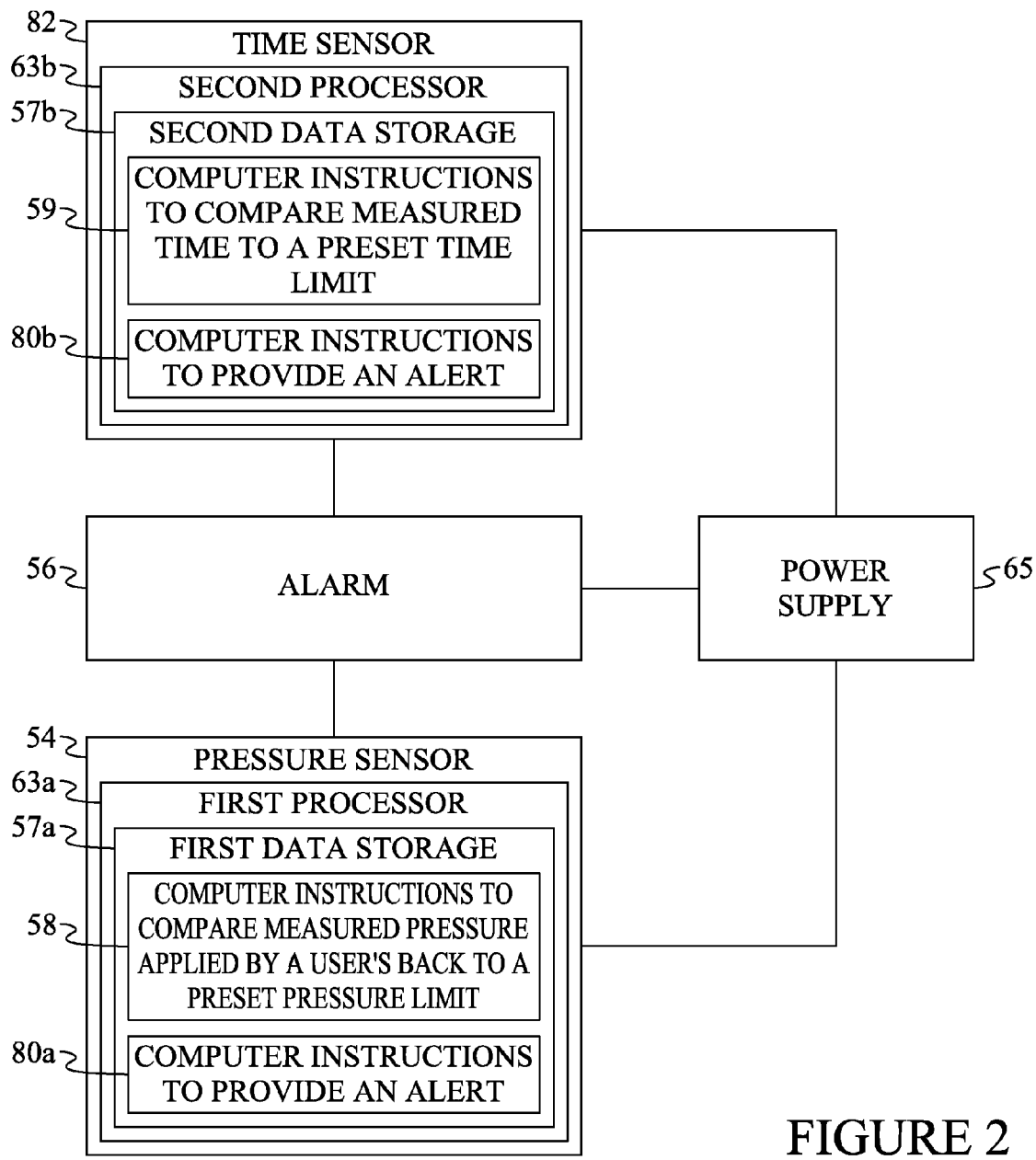
FIG. 2 shows an embodiment of a pressure sensor, a time sensor, an alarm, and a power supply.

FIG. 2 shows embodiments of a pressure sensor 54, a time sensor 82, and an alarm 56 usable with the method, each shown in communication with a power supply 65. The pressure sensor and the time sensor can each be in communication with the alarm. The power supply can be a battery or another source of electrical power.

The pressure sensor is shown having a first processor 63a and a first data storage 57a. Computer instructions are shown stored on the first data storage including: computer instructions to compare measured pressure applied by a user's back to a preset pressure limit 58 and computer instructions to provide an alert 80a when the pressure is greater than a preset limit.

The time sensor 82 is shown having a second processor 63b and a second data storage 57b. Computer instructions are shown stored on the second data storage including; computer instruction to compare measured time to a preset time limit 59 and computer instructions to provide an alert 80b when a usage time is greater than a preset limit.

Figure 3:
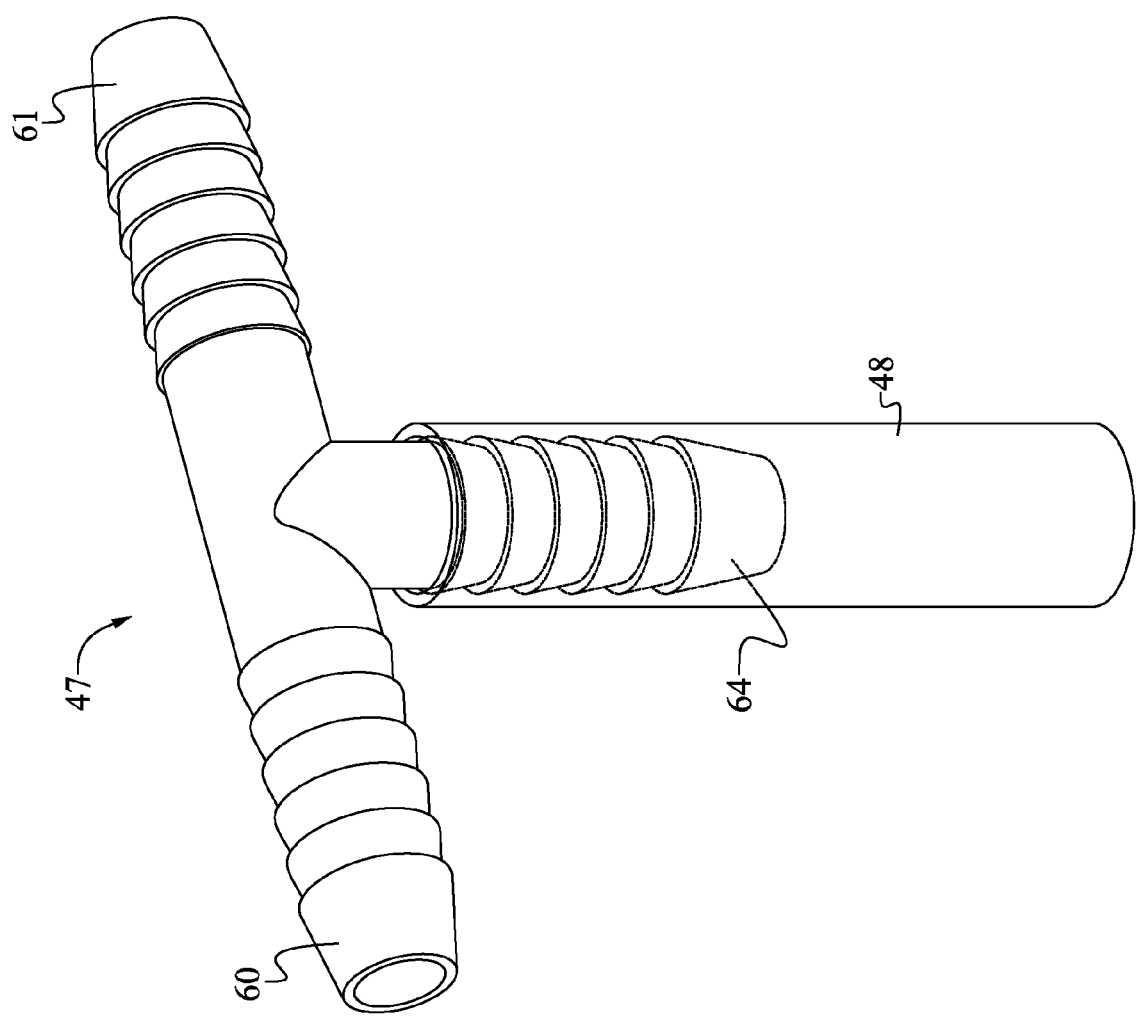
FIG. 3 shows a support member of a traction head.

FIG. 3 shows an embodiment of the support member 47 usable with the method having a left tube 60, a right tube 61, and a central tube 64. The centralizer 48 is shown disposed on the central tube.

Figure 4:
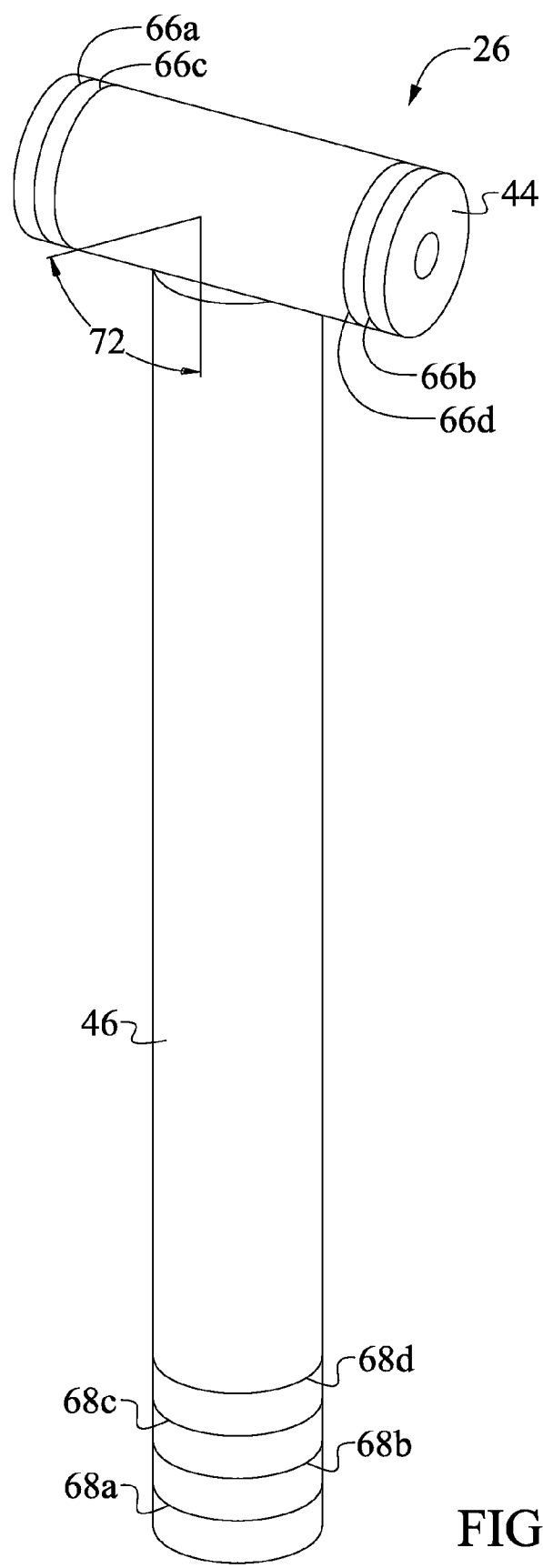
FIG. 4 shows a customizable traction device.

FIG. 4 shows an embodiment of a customizable traction device 26 usable with the method having a shearable traction head 44 and a shearable traction body 46.

The shearable traction head is shows with a plurality of traction head dimensional indicators 66a, 66b, 66c, and 66d. The shearable traction body is shown with a plurality of traction body dimensional indicators 68a, 68b, 68c, and 68d. An angle of engagement between the shearable traction head and the shearable traction body is shown, which can be a variable angle 72.

It is contemplated that the shearable traction head and body can each have more or less dimensional indicators.

Figure 5:
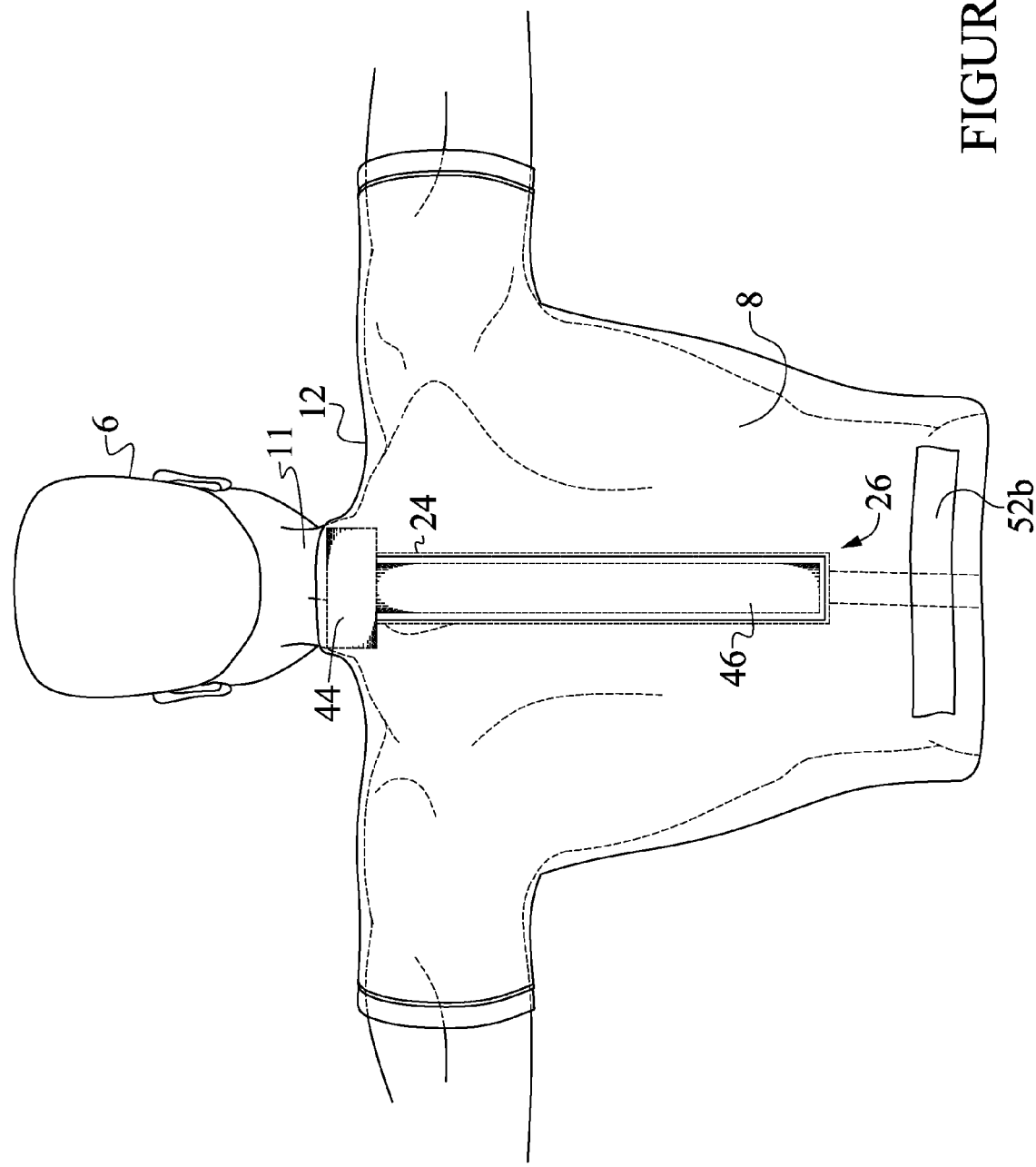
FIG. 5 shows a user with a wearable ambulatory traction system.

FIG. 5 shows a back view of a user 6 wearing a wearable ambulatory traction system usable with the method. The traction device 26 is shown disposed in a pouch 24. The pouch is disposed on an inside surface of a fabric garment 12 worn by the user.

The traction body 46 is shown disposed proximate a portion of the user's back 8; while the traction head 44 is shown disposed proximate a portion of the user's neck 11.

A message portion 52b is shown on the fabric garment.

Figure 6:
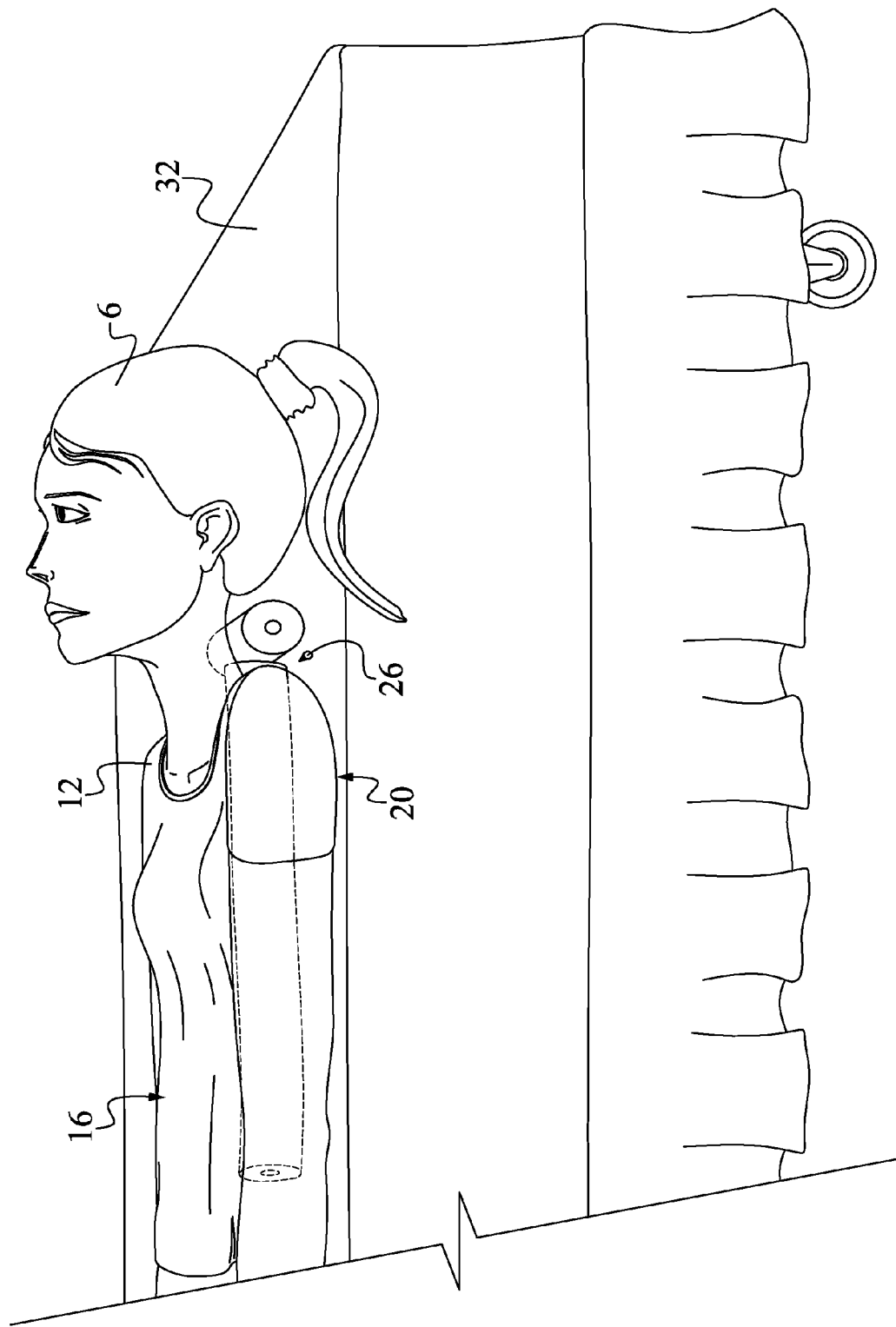
FIG. 6 shows a user with a wearable ambulatory traction system and a surface.

FIG. 6 shows a user 6 wearing a wearable ambulatory traction system. The traction device 26 is shown disposed between the user and a surface 32. The surface is shown here as a bed. The user is wearing a fabric garment 12. The fabric garment is shown having a front portion 16 and a back portion 20.

The traction device is shown engaged with the surface through the fabric garment. A pressure can be applied to the traction device from the user's back. The pressure applied to the traction device from the user's back can be transferred from the traction device to the surface, and an equal and opposite pressure can be transferred from the surface back to the traction device and to the user's back. The pressure applied from the traction device to the user's back can be a decompressive and therapeutic pressure.

Figure 7:
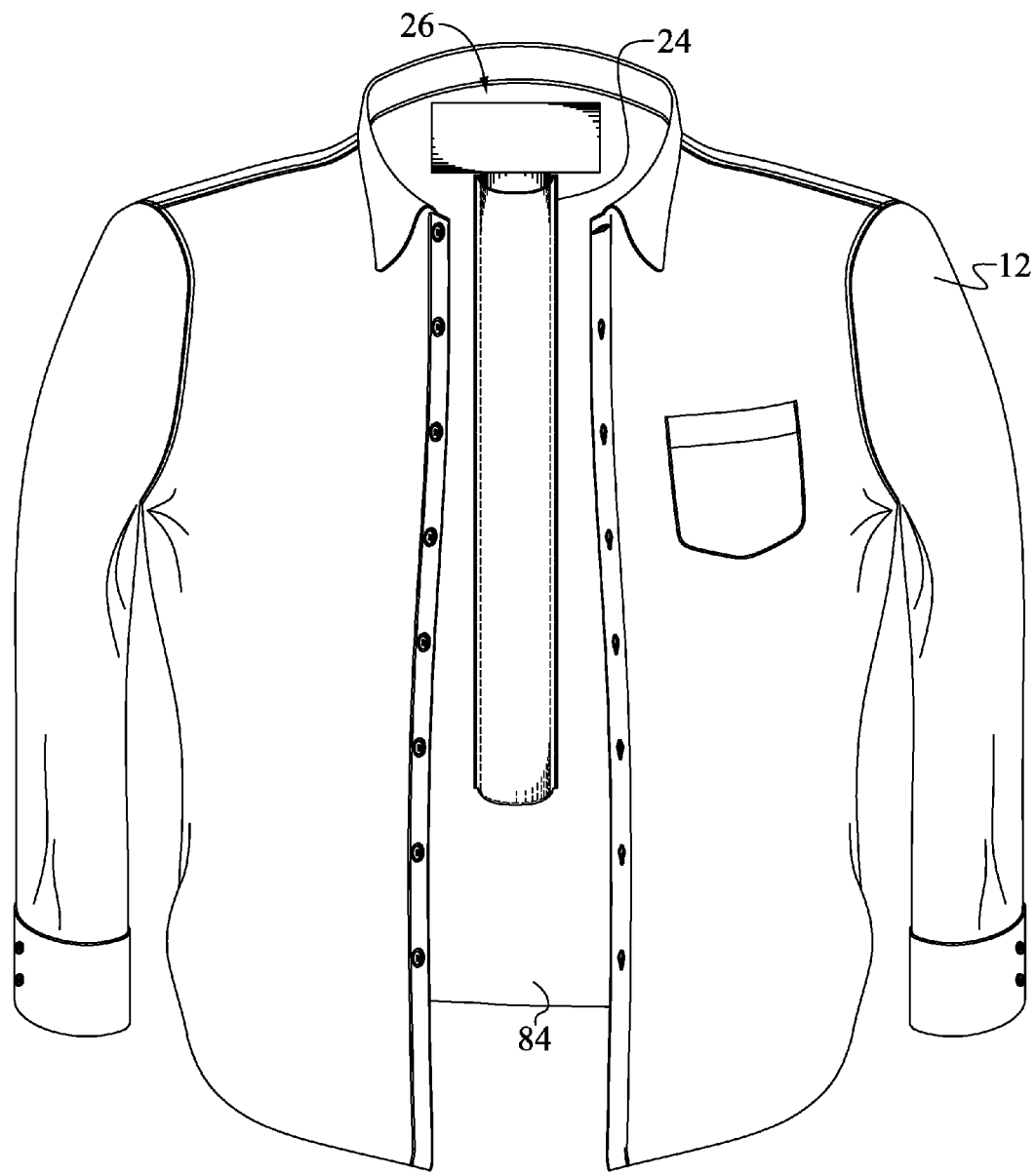
FIG. 7 shows a wearable ambulatory traction system.

FIG. 7 show an embodiment of a wearable ambulatory traction system usable with the method. A fabric garment 12 is shown having a pouch 24 secured to an inside surface 84 of the fabric garment. A traction device 26 is shown inserted within the pouch.

Figure 8:
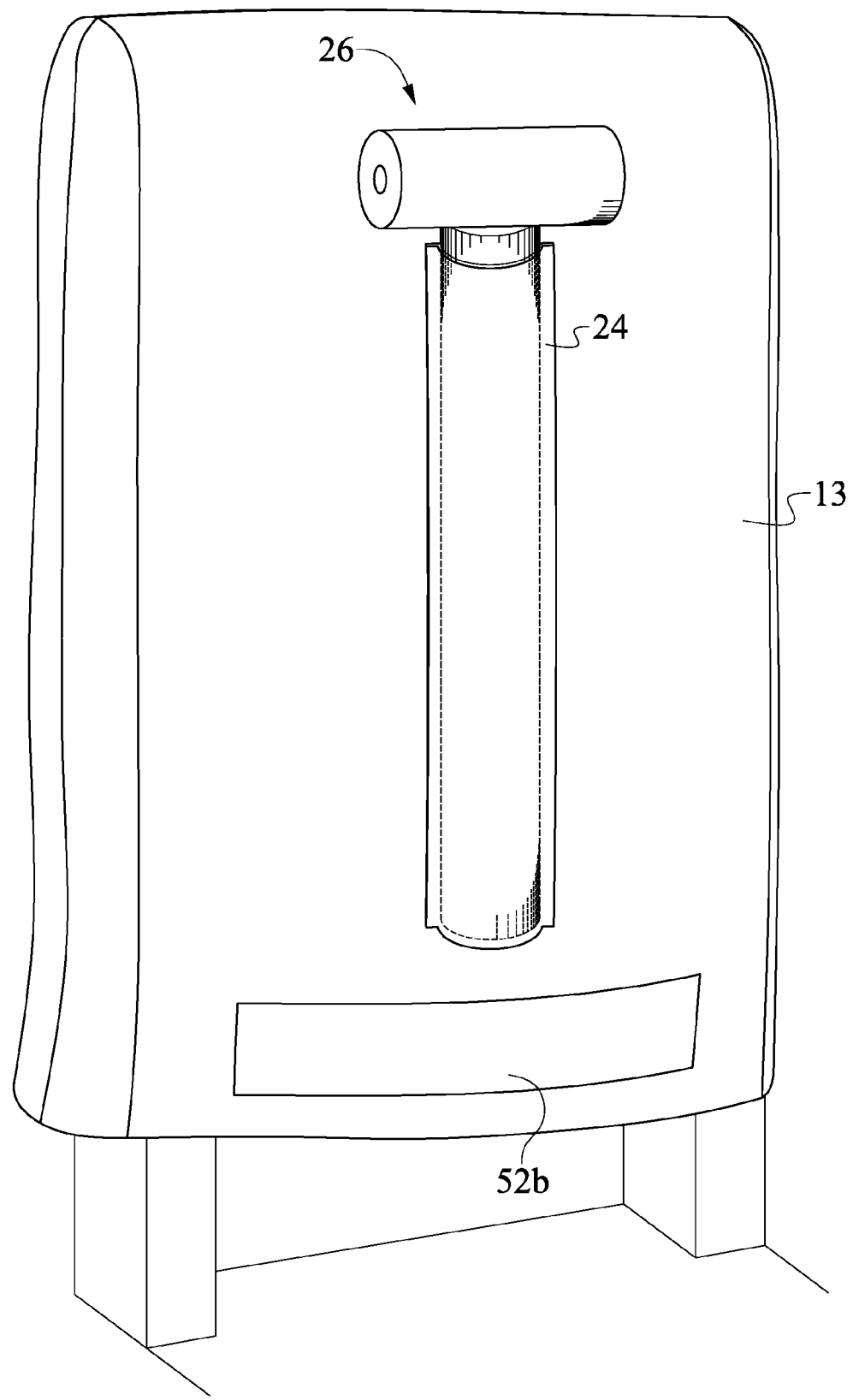
FIG. 8 shows a removable fraction system without a chair.

FIG. 8 shows a removable traction system usable with the method.

The traction device 26 is shown disposed in a pouch 24. The pouch 24 is disposed on an inside surface of a removable fabric chair cover 13.

A message portion 52b is shown on the removable fabric chair cover.

Figure 9:
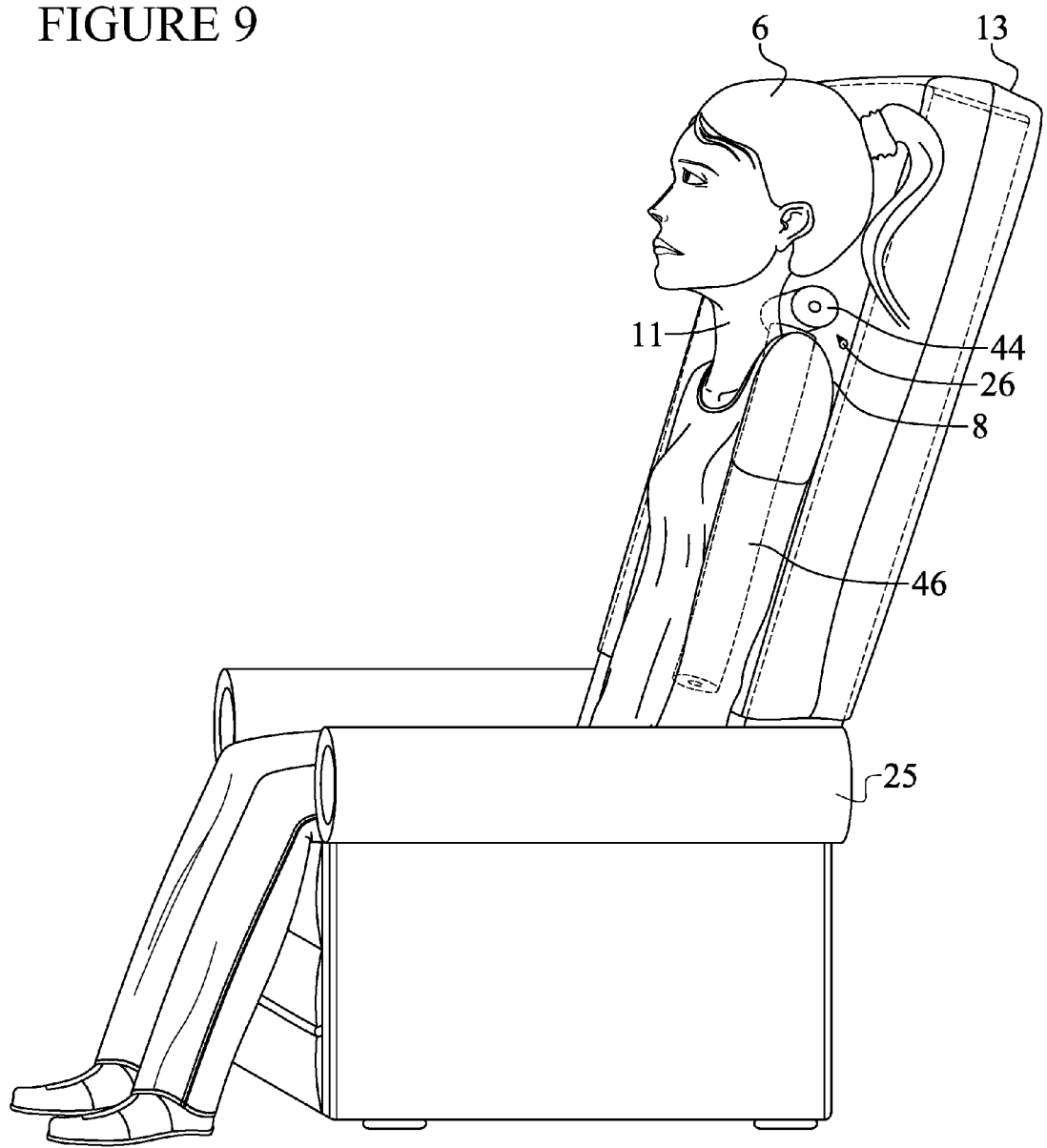
FIG. 9 shows a removable chair supported traction system.

FIG. 9 shows removable traction system usable with the method disposed on a chair 25. The removable fabric chair cover 13 is shown with the pouch 24.

A user 10 is shown sitting on the chair. The traction device is disposed between the chair and the user. The traction body 46 is shown disposed in the pouch and proximate a portion of the user's back 8; while the traction head 44 is shown disposed proximate a portion of the user's neck 11.

A pressure can be applied to the traction device from the user's back. The pressure applied to the traction device from the user's back can be transferred from the traction device to the chair, and an equal and opposite pressure can be transferred from the chair back to the traction device and to the user's back. The pressure applied from the traction device to the user's back can be a decompressive and therapeutic pressure.

Figure 10:
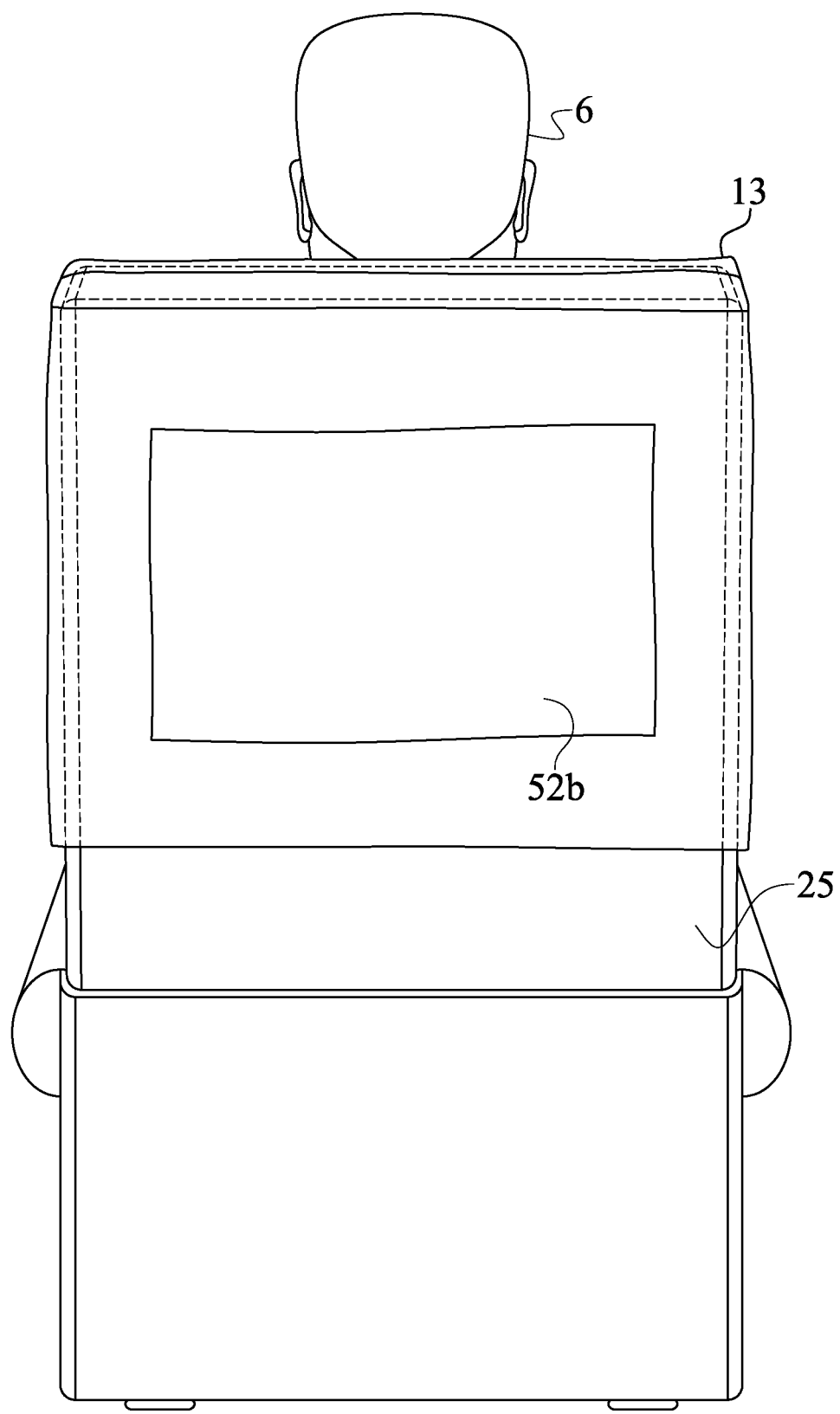
FIG. 10 shows a removable chair supported traction system and a user.

FIG. 10 shows a back view of a chair 25 with a removable fabric chair cover 13 disposed over the chair. A user 6 is shown disposed in the chair. A message portion 52b is shown disposed on the removable fabric chair cover.

Figure 11:
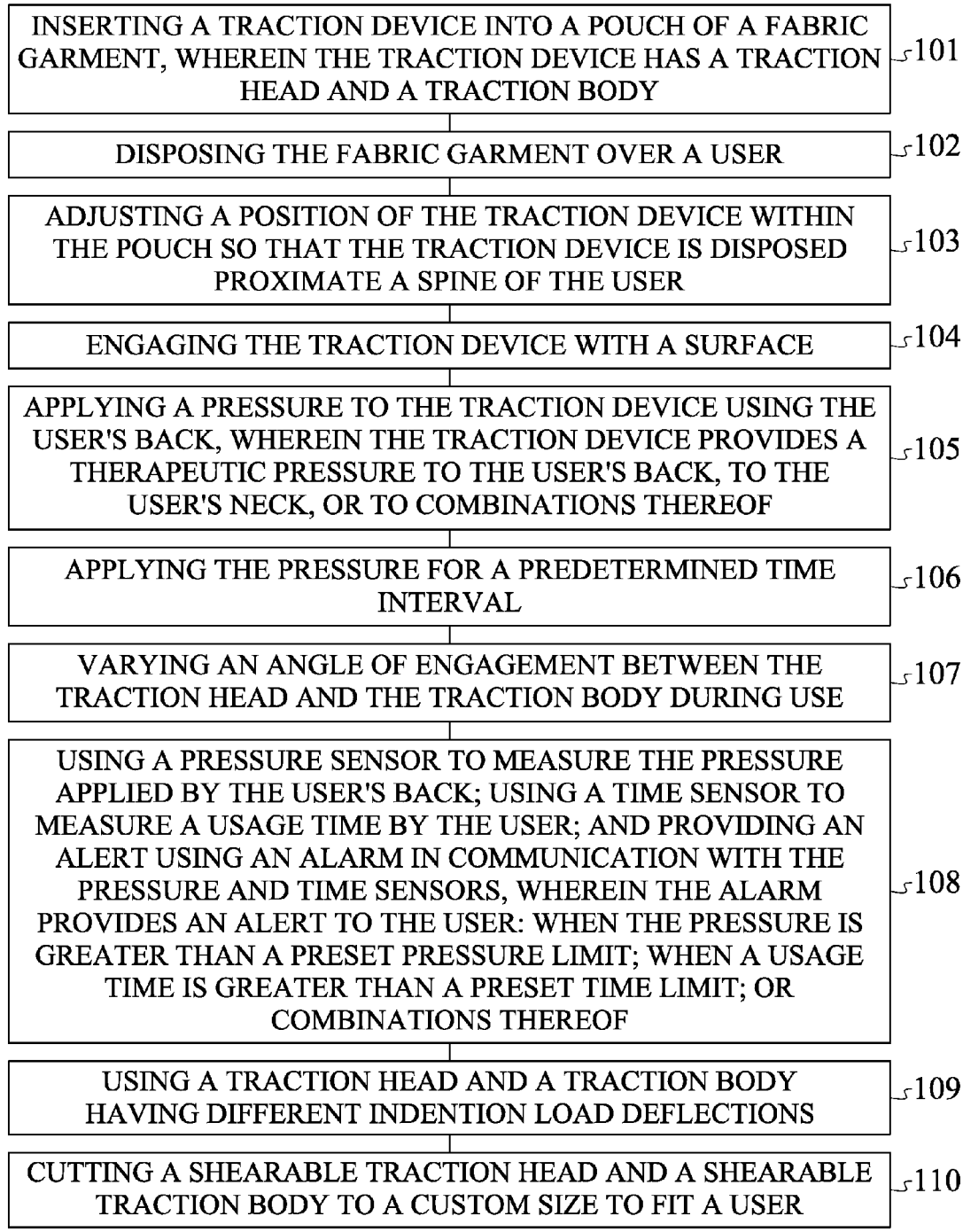
FIG. 11 shows a diagram of an illustrative embodiment of the method.

FIG. 11 shows a diagram showing illustrative steps of an embodiment of the method.

Step 101 can include inserting a traction device into a pouch of a fabric garment, wherein the traction device has a traction head and a traction body.

Step 102 can include disposing the fabric garment over a user.

Step 103 can include adjusting a position of the traction device within the pouch so that the traction device is disposed proximate a spine of the user.

Step 104 can include engaging the traction device with a surface.

Step 105 can include applying a pressure to the traction device using the user's back, wherein the traction device provides a therapeutic pressure to the user's back, to the user's neck, or to combinations thereof.

Step 106 can include applying the pressure for a predetermined time interval.

Step 107 can include varying an angle of engagement between the traction head and the traction body during use.

Step 108 can include using a pressure sensor to measure the pressure applied by the user's back; using a time sensor to measure a usage time by the user; and providing an alert using an alarm in communication with the pressure and time sensors, wherein the alarm provides an alert to the user: when the pressure is greater than a preset pressure limit; when a usage time is greater than a preset time limit; or combinations thereof.

Step 109 can include using a traction head and a traction body having different indention load deflections.

Embodiments can include step 110, which can be performed before step 101 as described above.

Step 110 can include cutting a shearable traction head and a shearable traction body to a custom size to fit a user.

The shearable traction head and body can be used in place of the traction head and body in the remaining steps of the method.

Figure 12A:
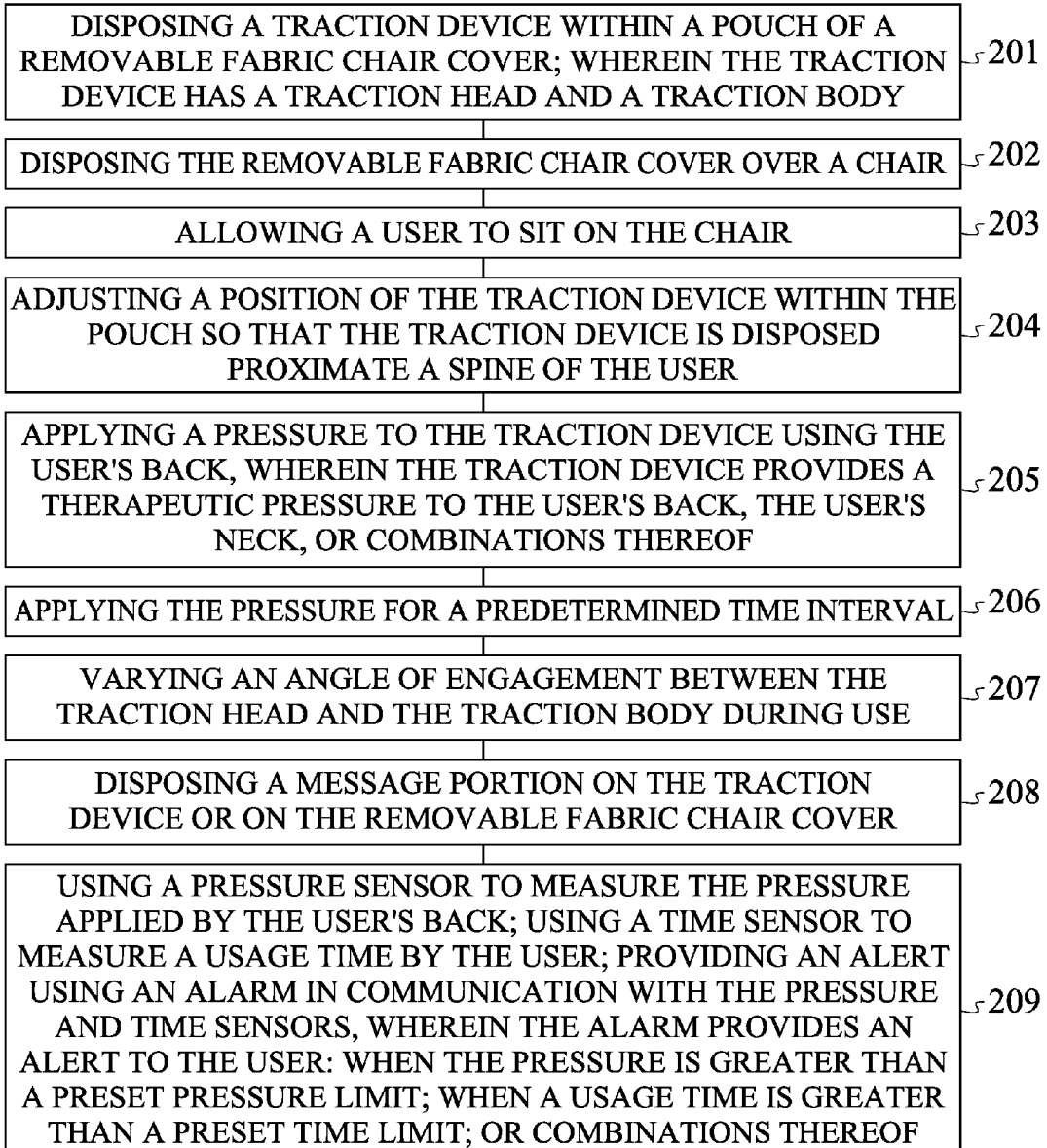

FIG. 12A shows an embodiment of a method for treating a user's back, a user's neck, or combinations thereof.

Step 201 can include disposing a traction device within a pouch of a removable fabric chair cover; wherein the traction device has a traction head and a traction body.

Step 202 can include disposing the removable fabric chair cover over a chair.

Step 203 can include allowing a user to sit on the chair.

Step 204 can include adjusting a position of the traction device within the pouch so that the traction device is disposed proximate a spine of the user.

Step 205 can include applying a pressure to the traction device using the user's back, wherein the traction device provides a therapeutic pressure to the user's back, the user's neck, or combinations thereof.

Step 206 can include applying the pressure for a predetermined time interval.

Step 207 can include varying an angle of engagement between the traction head and the traction body during use.

Step 208 can include disposing a message portion on the traction device or on the removable fabric chair cover.

Step 209 can include using a pressure sensor to measure the pressure applied by the user's back; using a time sensor to measure a usage time by the user; providing an alert using an alarm in communication with the pressure and time sensors, wherein the alarm provides an alert to the user: when the pressure is greater than a preset pressure limit; when a usage time is greater than a preset time limit; or combinations thereof.

FIG. 12B shows a continuation of FIG. 12A.

Embodiments can include step 210, which can be performed before step 201 as described above.

Step 210 can include using a traction head that is a shearable traction head, using a traction body that is a shearable traction body, cutting the shearable traction head and body to custom sizes to fit the user; and disposing the shearable traction body within the pouch.

The shearable traction head and body can be used in place of the traction head and body in the remaining steps of the method.

Step 211 can include using a traction head and a traction body having different indention load deflections.

While these embodiments have been described with emphasis on the embodiments, it should be understood that within the scope of the appended claims, the embodiments might be practiced other than as specifically described herein.

What is claimed is:

1. A method for treating a user's back, a user's neck, or combinations thereof, the method comprising the steps of:
  a. inserting a traction device into a pouch of a fabric garment, wherein the traction device comprises a traction head; a traction body; and a centralizer disposed within a first hole of the traction head and a second hole of the traction body, and wherein the centralizer connects the traction body with the traction head;
  b. disposing the fabric garment over a user;
  c. adjusting a position of the traction device within the pouch so that the traction device is disposed proximate a spine of the user;
  d. engaging the traction device with a surface; and
  e. applying a pressure to the traction device using the user's back, wherein the traction device provides a therapeutic pressure to the user's back, to the user's neck, or to combinations thereof.

2. The method of claim 1, wherein the surface is a bed.

3. The method of claim 1, further comprising the step of using the traction head and the traction body having different indention load deflections.

4. The method of claim 1, further comprising using the traction head and the traction body which are both cylindrically shaped and have identical diameters.

5. The method of claim 1, further comprising using the traction head with a diameter different from a diameter of the traction body.

6. The method of claim 1, further comprising the step of applying the pressure for a predetermined time interval.

7. The method of claim 6, wherein the predetermined time interval is from five minutes to thirty minutes after awaking from a sleep.

8. The method of claim 1, further comprising providing a message portion on the traction device or on the fabric garment.

9. The method of claim 1, further comprising the steps of:
  a. using a pressure sensor to measure the pressure applied by the user's back;
  b. using a time sensor to measure a usage time by the user; and
  c. providing an alert using an alarm in communication with the pressure and time sensors, wherein the alarm provides an alert to the user:
    i. when the pressure is greater than a preset pressure limit;
    ii. when a usage time is greater than a preset time limit; or
    iii. combinations thereof.

10. A method for treating a user's back, a user's neck, or combinations thereof, the method comprising the steps of:
  a. disposing a traction device within a pouch of a removable fabric chair cover; inserting a traction device into a pouch of a fabric garment wherein the traction device has a traction head and a traction body, and wherein the traction device comprises a centralizer disposed within a first hole of the traction head and a second hole of the traction body, and wherein the centralizer connects the traction body with the traction head;
  b. disposing the removable fabric chair cover over a chair;
  c. allowing a user to sit on the chair;
  d. adjusting a position of the traction device within the pouch so that the traction device is disposed proximate a spine of the user; and
  e. applying a pressure to the traction device using the user's back, wherein the traction device provides a therapeutic pressure to the user's back, the user's neck, or combinations thereof.

11. The method of claim 10, further comprising the step of applying the pressure for a predetermined time interval.

12. The method of claim 10, further comprising disposing a message portion on the traction device or on the removable fabric chair cover.

13. The method of claim 10, further comprising the steps of:
- a. using a pressure sensor to measure the pressure applied by the user's back;
- b. using a time sensor to measure a usage time by the user; and
- c. providing an alert using an alarm in communication with the pressure and time sensors, wherein the alarm provides an alert to the user:
  - i. when the pressure is greater than a preset pressure limit;
  - ii. when a usage time is greater than a preset time limit; or
  - iii. combinations thereof.

14. The method of claim 10, wherein the traction head is a shearable traction head and the traction body is a shearable traction body, the method further comprising the steps of:
- a. cutting the shearable traction head to a custom size to fit the user;
- b. cutting the shearable traction body to a custom size to fit the user;
- c. disposing the shearable traction body within the pouch; and
- d. applying a pressure to the shearable traction body and the shearable traction head using the user's back, wherein the shearable traction body and the shearable traction head provide a therapeutic pressure to the user's back, the user's neck, or combinations thereof.

15. The method of claim 10, further comprising the step of using the traction head and the traction body having different indention load deflections.

* * * * *